(12) United States Patent
Zhang et al.

(10) Patent No.: US 11,255,846 B2
(45) Date of Patent: Feb. 22, 2022

(54) REAGENT MIXING AND CONVEYING DEVICE AND REAGENT MIXING METHOD

(71) Applicant: LEADWAY (HK) LIMITED, Hong Kong (CN)

(72) Inventors: Hao Zhang, Hong Kong (CN); Yigang Yang, Hong Kong (CN); Jianfei Zheng, Hong Kong (CN); Gang Wu, Hong Kong (CN)

(73) Assignee: Leadway (HK) Limited, Hong Kong (CN)

( * ) Notice: Subject to any disclaimer, the term of this patent is extended or adjusted under 35 U.S.C. 154(b) by 274 days.

(21) Appl. No.: 16/680,216

(22) Filed: Nov. 11, 2019

(65) Prior Publication Data

US 2020/0080993 A1  Mar. 12, 2020

Related U.S. Application Data

(63) Continuation of application No. 15/446,980, filed on Mar. 1, 2017, now Pat. No. 10,473,650.

(51) Int. Cl.
*G01N 35/04* (2006.01)
*G01N 35/10* (2006.01)
(Continued)

(52) U.S. Cl.
CPC ....... *G01N 33/5302* (2013.01); *B01F 9/0001* (2013.01); *B01F 9/0021* (2013.01);
(Continued)

(58) Field of Classification Search
CPC .......... G01N 33/5302; G01N 35/1002; G01N 35/04; G01N 1/38; G01N 2035/00524;
(Continued)

(56) References Cited

U.S. PATENT DOCUMENTS 3,627,276 A  12/1971  Gilford
5,244,633 A   9/1993  Jakubowicz et al.
(Continued)

FOREIGN PATENT DOCUMENTS

CN  2632680 Y  8/2004
CN  1667419 A  9/2005
(Continued)

OTHER PUBLICATIONS

Bearing Industry Vocational Training Series Material, Basic knowledge of rolling bearings. China Bearing Industry Association Compilation, Human Resources Staff Education Committee. Henan People's Publishing House, Aug. 2006 1st Edition:pages 5-6—incl machine generated Engl lang transl (8 pages total).

(Continued)

*Primary Examiner* — Jennifer Wecker
(74) *Attorney, Agent, or Firm* — Acuity Law Group, PC; Michael A. Whittaker (57) ABSTRACT

The present invention provides a reagent mixing device, which comprises a driving device, a transport device and a rotating part, wherein the transport device comprises a conveying mechanism for conveying a reagent kit and a mixing mechanism for mixing a reagent; the conveying mechanism is driven by the driving device to move relative to the mixing mechanism; the rotating part and mixing mechanism are in transmission matching; the conveying mechanism and the mixing mechanism are sleeved with each other to form a bearing structure. The present invention further provides a reagent mixing method. The reagent mixing device is small in size, smart in structure, easy to assemble and low in manufacturing cost. The reagent mixing method provided by the present invention is simple and reliable, high in overall operation reliability, and has very high application values in such analysis and test fields as (Continued)

full-automatic chemiluminescence immunoassay analyzers and biochemical analyzers.

11 Claims, 9 Drawing Sheets

(51) Int. Cl.
  *B01F 9/00* (2006.01)
  *G01N 35/02* (2006.01)
  *G01N 35/00* (2006.01)
  *B01F 9/10* (2006.01)
  *G01N 33/53* (2006.01)
  *G01N 1/38* (2006.01)

(52) U.S. Cl.
  CPC ............... *B01F 9/10* (2013.01); *G01N 1/38* (2013.01); *G01N 35/04* (2013.01); *G01N 35/1002* (2013.01); *G01N 35/025* (2013.01); *G01N 35/10* (2013.01); *G01N 2001/386* (2013.01); *G01N 2035/00465* (2013.01); *G01N 2035/00524* (2013.01); *G01N 2035/0443* (2013.01); *G01N 2035/0486* (2013.01)

(58) Field of Classification Search
  CPC ............... G01N 35/10; G01N 35/025; G01N 2035/00465; G01N 2035/0443; G01N 2035/0486; G01N 2001/386; B01F 9/0001; B01F 9/0021; B01F 9/10
  See application file for complete search history.

(56) References Cited

U.S. PATENT DOCUMENTS

| | | | |
|---|---|---|---|
| 5,314,825 | A | 5/1994 | Weyrauch et al. |
| 7,322,525 | B2 | 1/2008 | Itoh |
| 7,628,954 | B2 | 12/2009 | Gomm et al. |
| 8,864,030 | B2 | 10/2014 | Ohmae |
| 10,473,650 | B2 | 11/2019 | Zhang et al. |
| 2007/0062583 | A1 | 3/2007 | Cox et al. |
| 2012/0115213 | A1 | 5/2012 | Hofstadler et al. |
| 2018/0252707 | A1 | 9/2018 | Zhang et al. |

FOREIGN PATENT DOCUMENTS

| | | |
|---|---|---|
| CN | 200947103 Y | 9/2007 |
| CN | 201434871 Y | 3/2010 |
| CN | 201940244 U | 8/2011 |
| CN | 102192990 A | 9/2011 |
| CN | 101799478 B | 8/2012 |
| CN | 102128939 B | 10/2012 |
| CN | 102147370 B | 10/2012 |
| CN | 102830221 A | 12/2012 |
| CN | 103217540 A | 7/2013 |
| CN | 203170251 U | 9/2013 |
| CN | 102590350 B | 12/2013 |
| CN | 103675305 A | 3/2014 |
| CN | 203519619 U | 4/2014 |
| CN | 103472242 B | 10/2014 |
| CN | 104107647 A | 10/2014 |
| CN | 204480264 U | 7/2015 |
| CN | 104971647 A | 10/2015 |
| CN | 105510613 A | 4/2016 |
| JP | H07260794 A | 10/1995 |
| WO | 9716734 A1 | 5/1997 |
| WO | 0031535 A2 | 6/2000 |

OTHER PUBLICATIONS

First Office Action issued by SIPO in Chinese Patent Application No. 201510964321.8 dated Jul. 21, 2017—incl machine generated Engl lang transl.
First Office Action issued by SIPO in Chinese Patent Application No. 201510969391.2 dated Mar. 23, 2017—incl machine generated Engl lang transl.
First Office Action issued by SIPO in Chinese Patent Application No. 201521070844.X dated Apr. 12, 2016—incl machine generated Engl lang transl.
First Office Action issued by SIPO in Chinese Patent Application No. 201510961493.X dated May 16, 2017—machine generated Engl lang transl only.
First Office Action issued by SIPO in Chinese Patent Application No. 201510971531.X dated Oct. 25, 2016 2017—incl machine generated Engl lang transl.
First Office Action issued by SIPO in Chinese Patent Application No. 201510970251.7 dated Nov. 30, 2016—incl machine generated Engl lang transl.
Response for First Office Action issued by SIPO in Chinese Patent Application No. 201510964321.8 dated Nov. 28, 2017—incl machine generated Engl lang transl.
Response for First Office Action issued by SIPO in Chinese Patent Application No. 201510969391.2 dated Mar. 18, 2017—incl machine generated Engl lang transl.
Response for First Office Action issued by SIPO in Chinese Patent Application No. 201521070844.X dated Sep. 15, 2016—incl machine generated Engl lang transl.
Response for First Office Action issued by SIPO in Chinese Patent Application No. 201510971531.X dated Aug. 15, 2017—incl machine generated Engl lang transl.
Response for First Office Action issued by SIPO in Chinese Patent Application No. 201510970251.7 dated May 14, 2017—incl machine generated Engl lang transl.
Response for Second Office Action issued by SIPO in Chinese Patent Application No. 201510971531.X dated Nov. 28, 2017—incl machine generated Engl lang transl.
Response for Third Office Action issued by SIPO in Chinese Patent Application No. 201510971531.X dated Jul. 1, 2018—incl machine generated Engl lang transl.
Response to First Office Action issued in Chinese Patent Application No. 201510961493.X dated Sep. 18, 2017—incl machine generated Engl lang transl.
Response to Second Office Action issued in Chinese Patent Application No. 201510961493.X dated May 11, 2018—incl machine generated Engl lang transl.
Response to Third Office Action issued in Chinese Patent Application No. 201510961493.X dated Mar. 11, 2019—incl machine generated Engl lang transl.
Second Office Action issued by SIPO in Chinese Patent Application No. 201510971531.X dated Sep. 18, 2017—incl machine generated Engl lang transl.
Second Office Action issued by SIPO in Chinese Patent Application No. 201510961493.X dated Feb. 28, 2018—incl machine generated Engl lang transl.
Third Office Action issued by SIPO in Chinese Patent Application No. 201510971531.X dated Apr. 17, 2018—incl machine generated Engl lang transl.
Third Office Action issued by SIPO in Chinese Patent Application No. 201510961493.X dated Dec. 28, 2018—incl machine generated Engl lang transl.

REAGENT MIXING AND CONVEYING DEVICE AND REAGENT MIXING METHOD

CROSS-REFERENCE TO RELATED APPLICATIONS

The present invention is a continuation of U.S. patent application Ser. No. 15/446,980, filed Mar. 1, 2017, now U.S. Pat. No. 10,473,650, which is hereby incorporated in its entirety by reference.

FIELD OF THE INVENTION

The present invention relates to a reagent mixing device and a reagent mixing method, in particular to a reagent mixing and conveying device for a chemiluminescence immunoassay analyzer.

BACKGROUND OF THE INVENTION

A full-automatic test analyzer is capable of automatically performing a series of operation steps including sample addition, reagent addition, reaction, test, test result acquisition and the like. It is now very common to determine the content of a component in a sample under test by using a full-automatic detection analyzer, for example, a full-automatic chemiluminescence immunoassay analyzer which includes a sample cabin, a reagent cabin, a reaction cabin and a test cabin. The test process of the analyzer generally comprises the following steps: first, putting a sample and a reagent into the sample cabin and the reagent cabin respectively; next, adding the sample and the reagent into a cuvette; then, making the cuvette go through systems of incubation, separation, washing and the like; and finally, feeding the cuvette into a closed dark chamber and completing the test.

Chemiluminescence immunoassay (CLIA) is an analysis technique through which a chemiluminescence testing technique with high sensitivity is combined with immunoreaction with high specificity to quantitatively detect various antigens, haptens, antibodies, hormones, enzymes, fatty acids, vitamins, medicines and the like. Chemiluminescence immunoassay needs multiple reagents, including solid-phase reagents, and a common solid-phase reagent is marked magnetic particles. When in use, the magnetic particle reagents are required to be uniform in concentration. However, the magnetic particles are apt to deposit under the effect of gravity, resulting in nonuniformity. If the magnetic particle reagents participate in relevant reactions after deposition, the stability and reliability of testing results can be severely affected. Therefore, the magnetic particle reagents need to be uniformly mixed before use.

In an existing full-automatic chemiluminescence immunoassay analyzer, a stirring mechanism is used to stir and uniformly mix the magnetic particle reagents. However, this method is not only long in mixing time and poor in effect, but also very liable to cause cross pollution. If a high-frequency throughout or oscillation method is used to mix the magnetic particle reagents, the requirement that the magnetic particle reagents in a plurality of reagent kits should be simultaneously mixed cannot be met, and the test speed of the full-automatic analyzer can be lowered. In the method that the magnetic particle reagents are mixed in a transmission matching manner, an analysis instrument comprises a reagent kit conveying part and a magnetic particle reagent mixing part. By adopting a full-automatic analyzer, a corresponding reagent kit can be conveyed to a reagent acquisition position of the analyzer by the conveying part according to the demands of test items, and in the reagent kit conveying process, the magnetic particle reagents are uniformly mixed by the mixing part in a transmission matching manner. However, in an existing design, the conveying part and the mixing part belong to independent operation systems. Due to relatively independent and separated structures, the operation accuracy and reliability of the analyzer can be degraded, and the assembling complexity and the production and manufacturing costs of the analyzer can be increased. The size of the analyzer itself can also be increased due to complex and diverse modules of a mechanical structure, so that the analyzer is very large, and a relatively large space is needed in a laboratory.

In the existing full-automatic detection analyzer, the matching between a reagent kit and a reagent kit bracket generally needs complex matching structures such as a hook to keep the reagent kit in place on the reagent kit bracket. Therefore, the manufacture of the reagent kit and the reagent kit bracket is not only time consuming, but also high in cost. The reagent kit and the reagent kit bracket are incompact in structure and large in size. Mechanical noise can be generated from assembled fittings, so that the test precision of the analyzer can be affected, and moreover, subsequent repairing difficulties and cost can be increased.

In the test analysis field, multiple reagents are generally needed to accomplish the test on one item. When the full-automatic test analyzer is adopted to test the item, multiple reagents are gathered in one reagent kit, and the reagent kit is put into the full-automatic analyzer. A plurality of reagent bottle storage cavities are formed in the reagent kit, and different reagents are contained in different reagent bottles. The reagent bottles filled with the reagents are put into the reagent kit storage cavities in advance.

When different items are tested, the reagent kit in the analyzer needs to be replaced. Or the reagent kit needs to be replaced if the reagents in the reagent kit are used up. If a reagent kit without a handle is used, an operator has to grasp the body of the reagent kit to take out the reagent kit. If reagent kits are closely placed inside the analyzer, that is, the reagent kits are arranged close to one another, then the space reserved for the operator to hold the reagent kits by fingers is small, and thus the reagent kits cannot be conveniently taken out. If the reagent kit is additionally provided with a handle, although the reagent kit can be very conveniently taken out by the operator, a certain space of the instrument will be occupied by the handle, and the overall size of the instrument is increased, so that not only is the material cost of the instrument increased, but also a relatively larger space of the laboratory will be occupied.

According to demands of medical test, a plurality of test items need to be carried out with one sample sometimes. For example, to analyze whether a patient has a communicable disease, items such as serial HSV-I, HSV-II, RV, HCMV and TOXO, Chlamydia, Gonorrhea, HIV and Syphilis in series HBsAg, HBsAb, HBeAg, HBeAb, HBcAb, HCV and ToRCH of a sample of the patient need to be tested. To analyze whether the sample of the patient has a tumor marker, PSA, Cyfra21-1, AFP, CEA, NSE, CA19-9, CA15-3, CA72-4, CA125, CA 50, ProGRP, Fer, TPS, GPC3 and the like need to be tested. To determine whether a patient under test has drug abuse, items such as MOP, AMP, BAR, COC, MET, THC, BZO, MDMA, MTD, OPI and PCP need to be tested. Different test reagents are needed for different test items. Therefore, the reagent cabin of the full-automatic analyzer needs to be capable of storing a sufficient number of reagent kits at one time to satisfy test requirements. If reagent kit storing positions of the reagent cabin are not adequate, in the same test series, such as test on infectious disease series, reagent kits of corresponding test items need to be put into the analyzer for test in different batches. First, reagent kits for testing HBsAg, HBsAb, HBeAg, HBeAb, HBcAb, HCV, Chlamydia and Gonorrhea are put into the analyzer, at this time, the reagent kit storing positions of the reagent cabin of the analyzer are completely occupied, and then test is started. After the first batch of items are tested, the reagent kits used in the first batch of test are taken out, and then test reagent kits of HSV-I, HSV-II, RV, HCMV, TOXO, Chlamydia, Gonorrhea, HIV and Syphilis of a ToRCH series are put in. Therefore, the analysis test progress is affected.

SUMMARY OF THE INVENTION

To solve the problems in the prior art, the present invention provides a reagent mixing and conveying device which comprises a driving device, a transport device and a rotating part, wherein the transport device comprises a conveying mechanism for conveying a reagent kit and a mixing mechanism for mixing a reagent; the conveying mechanism is driven by the driving device to move relative to the mixing mechanism; the rotating part and the mixing mechanism are in transmission matching; and the conveying mechanism and the mixing mechanism are sleeved with each other to form a bearing structure.

Further, the conveying mechanism and the mixing mechanism are of annular structures; and the conveying mechanism is arranged inside a central hole of the mixing mechanism.

Further, the driving device comprises a driving motor and a driving end; and the driving end is arranged in a central hole of the conveying mechanism.

Further, the transmission mode between the driving end and the conveying mechanism is selected from gear engagement transmission, friction transmission and belt pulley transmission; and the transmission mode between the mixing mechanism and the rotating part is selected from gear engagement transmission and friction transmission.

Further, the conveying mechanism is of an internal gear structure; the mixing mechanism is of an external gear structure; the driving end is provided with a driving rack; the driving rack is engaged with the internal gear of the conveying mechanism; the rotating part is a gear; and the gear as the rotating part is engaged with the external gear of the mixing mechanism.

Further, the conveying mechanism comprises a base and a mounting seat; the base and the mixing mechanism are connected with each other in the form of a bearing; the mounting seat is mounted on the base; and the mounting seat comprises a transmission part matched with the driving device.

The present invention further provides a test reagent mixing method which comprises the following steps:

(1) providing a reagent mixing and conveying device;

(2) putting a reagent kit filled with a reagent to be mixed on the reagent mixing and conveying device;

(3) starting the reagent mixing and conveying device to uniformly mix the reagent;

wherein the reagent mixing and conveying device comprises a driving device, a transport device and a rotating part; the transport device comprises a conveying mechanism for conveying a reagent kit and a mixing mechanism for mixing a reagent; the driving device comprises a driving motor and a driving end; the driving end is arranged in a central hole of the conveying mechanism; the conveying mechanism is driven by the driving device to move relative to the mixing mechanism; the rotating part and the mixing mechanism are in transmission matching; the rotating part is used for stirring reagent to be mixed; and the conveying mechanism and the mixing mechanism are sleeved with each other to form a bearing structure.

Further, the conveying mechanism and the mixing mechanism are of annular structures; and the conveying mechanism is arranged in a central hole of the mixing mechanism.

Further, the conveying mechanism is of an internal gear structure; the mixing mechanism is of an external gear structure; the driving end is provided with a driving rack; the driving rack is engaged with the internal gear of the conveying mechanism; the rotating part is a gear; and the gear as the rotating part is engaged with the external gear of the mixing mechanism.

Further, the conveying mechanism is driven by the driving device to move relative to the mixing mechanism; a corresponding reagent kit is conveyed to a reagent acquisition position of an analyzer by the conveying mechanism; meanwhile, with the rotation of the conveying mechanism, the rotating part for uniformly mixing the reagent is in transmission with the mixing mechanism; and a reagent bottle autorotates inside the reagent kit under the transmission of the mixing mechanism and the rotating part, so that the reagent inside the reagent bottle is uniformly mixed under rotation.

The reagent mixing and conveying device provided by the present invention is small in size, smart in structure, simple and reliable, easy to assemble, high in overall operation reliability and low in manufacturing cost. In addition, the mixing method of the magnetic particles of the present invention is simple and reliable, good in mixing effect, free of cross pollution risk, and moreover, a plurality of magnetic particle agents can be uniformly mixed simultaneously.

By adopting the test reagent storage device provided by the present invention, the space is effectively utilized, and the reagent storage amount is increased. For the reagent kit and the reagent kit bracket, due to the matching between positioning parts and positioning slots, the reagent kit can be more firmly placed inside reagent cabin. Such a matching mechanism can effectively reduce shaking of the reagent kit and lower the noise of the analyzer.

Due to the matching structure of clamping parts of the reagent bottle and the reagent kit, a reagent kit body can also be lifted while the reagent bottle is lifted up, so that the whole reagent kit body is kept in balance, and the risk that the reagent is dumped because of inclination is avoided.

DETAILED DESCRIPTION OF THE EMBODIMENTS

The present invention is further described in detail below in conjunction with accompanying drawings and embodiments, but the protection scope of the invention is not limited thereto.

Figure 20:
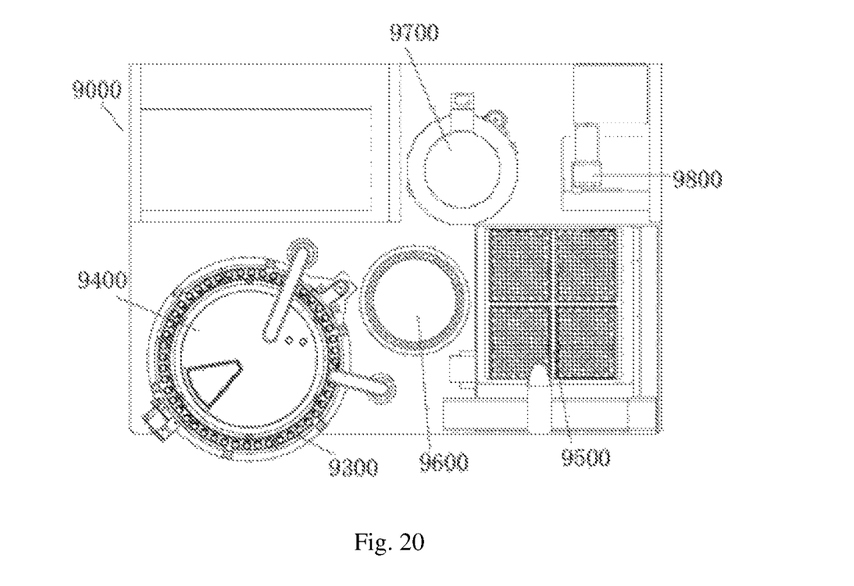
FIG. 20 is a schematic diagram of an internal structure of a full-automatic chemiluminescence immunoassay analyzer.
Figure 21:
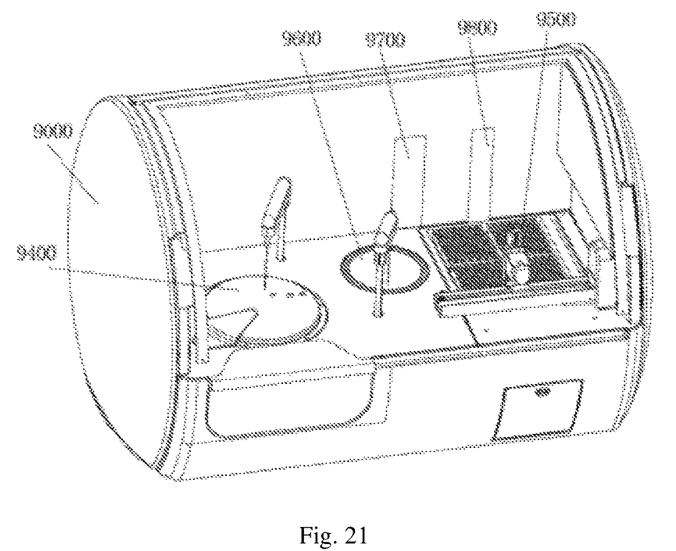
FIG. 21 is a schematic diagram of a full-automatic chemiluminescence immunoassay analyzer.
Figure 22:
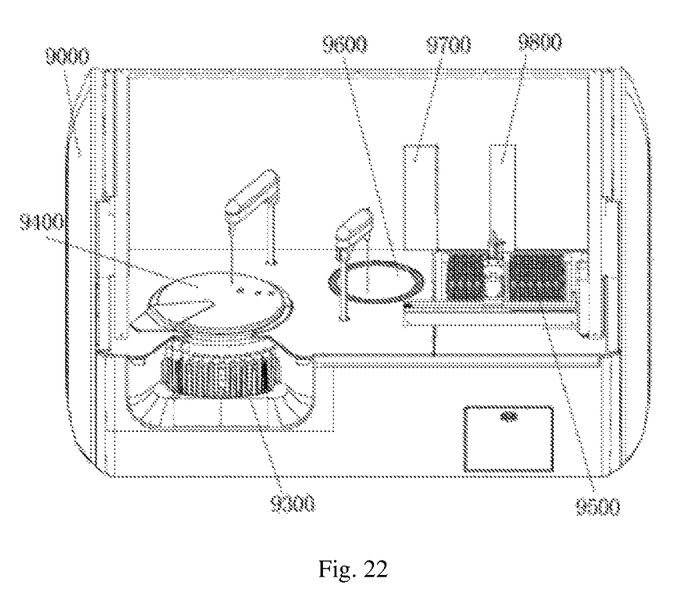
FIG. 22 is a full-automatic chemiluminescence immunoassay analyzer without a sample cabin side baffle plate.

A full-automatic chemiluminescence immunoassay analyzer 9000, as shown in FIGS. 20 to 22, includes a sample cabin 9300, a reagent cabin 9400, a cuvette storage cabin 9500, an incubation cabin 9600, a washing cabin 9700 and a test cabin 9800. To analyze components of a sample under test, firstly, a sample and a reagent are respectively put into the sample cabin and the reagent cabin; a cuvette is taken out of the cuvette storage cabin 9500 of the full-automatic chemiluminescence immunoassay analyzer, and is put into the incubation cabin; next, the sample and the reagent are put into the cuvette according to preset procedures, and an incubation procedure and a washing procedure are implemented; finally, the cuvette is fed into the test cabin to complete sample component analysis. The sample cabin herein includes an identity information reading device; and the reagent cabin includes a reagent mixing and conveying device.

Figures 1, 2:
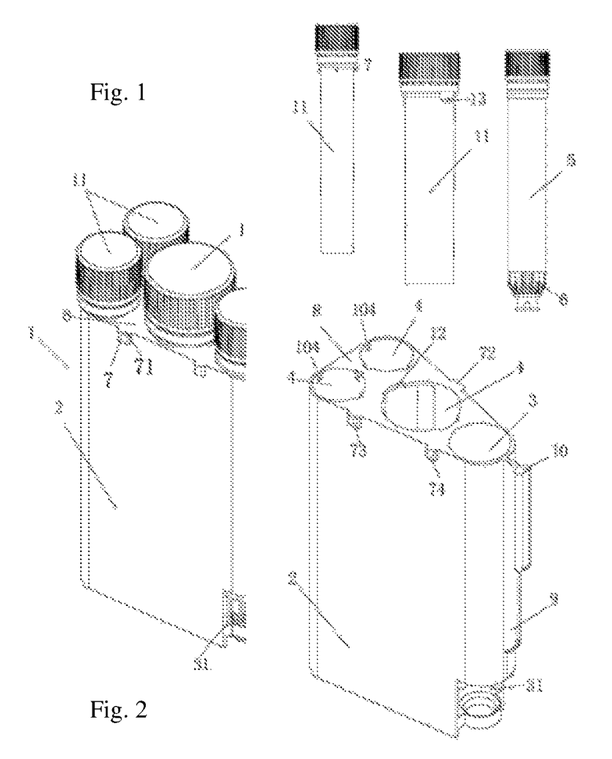
FIG. 1 is a schematic diagram of a reagent kit body and reagent bottles separated from each other.
FIG. 2 is a schematic diagram of the reagent kit body and the reagent bottles assembled together.

As shown in FIGS. 1 and 2, a reagent kit 1 for storing a test reagent includes a kit body 2 and a mixing cavity 3; the mixing cavity 3 is used for storing the reagent to be mixed uniformly during test; the reagent can be directly fed into the mixing cavity or fed into a reagent bottle in advance and subsequently put into the mixing cavity 3. If necessary, the reagent kit may further include storage cavities 4, which are used for storing reagents with relatively low requirement on uniform mixing during test, and the reagents can be directly fed into the storage cavities, or are fed into reagent bottles in advance and subsequently put into the storage cavities 4.

In an embodiment of FIG. 1, the reagent to be uniformly mixed is fed into a mixing reagent bottle 5 in advance; the mixing reagent bottle 5 is provided with a rotating part 6. The mixing reagent bottle 5 filled with the reagent is put into the mixing cavity 3 of the reagent kit. With rotation of the rotating part 6, the mixing reagent bottle 5 is caused to rotate inside the mixing cavity 3, so that the reagent inside the mixing reagent bottle 5 enters a suspension mixing state due to rotation. The rotating part 6 can be a structure built in the mixing reagent bottle 5; that is, as shown in FIG. 1, the rotating part 6 has already been mounted on the mixing reagent bottle 5 before the mixing reagent bottle 5 is put into the mixing cavity. The rotating part 6 can also be a separate member; after the mixing reagent bottle 5 is put into the mixing cavity 3, the mixing reagent bottle cooperates with the rotating part, so that the mixing reagent bottle 5 and the rotating part 6 are assembled together. When being used as a separate part, the rotating part can be mounted on the reagent kit, or arranged on an instrument used with the reagent kit. In an embodiment of FIG. 2, after the mixing reagent bottle 5 is put into the mixing cavity 3, the rotating part 6 is positioned at a notch 31 of the mixing cavity 3.

A positioning hole 104 is formed in the wall of each reagent kit storage cavity and/or the mixing cavity; a positioning part 7 is correspondingly arranged on the tube wall of a reagent bottle 11. Before the reagent bottle is put into the storage cavity and/or the mixing cavity, the reagent bottle positioning part 7 is firstly aligned to the positioning slot 104, and subsequently, the reagent bottle is fed into a admission cavity and/or the mixing cavity downwards, thus ensuring that the reagent bottle can be accurately placed inside the admission cavity and/or the mixing cavity. The upper surface of the positioning part 7 is flush with that of the reagent bottle; the depth of the positioning slot 104 is identical to the longitudinal depth of the positioning part 7. After the positioning part of the reagent bottle is inserted along the positioning slot, if the upper surface of the positioning part is flush with that of the positioning slot, it means that the reagent bottle has been accurately positioned in place.

In another embodiment, the inner wall of each storage cavity also has an elastic piece for tightly clamping a reagent bottle inside the storage cavity.

In the test field, such as chemiluminescence immunoassay, multiple reagents are needed to accomplish the test of one item, including reagents with solid phases, such as reagents with magnetic particles. Therefore, the reagent kit with the mixing cavity 3 and a plurality of storage cavities 4 is adopted, and reagents with magnetic particles are put into the mixing reagent bottles.

During test, a reagent kit corresponding to a test item is put into an analyzer. In one embodiment, the analyzer includes a reagent kit bracket for holding the reagent kit, and according to type of test item, a corresponding test reagent kit is put in a corresponding position of the reagent kit bracket, and thus multiple items can be tested by starting the analyzer once.

Figure 3:
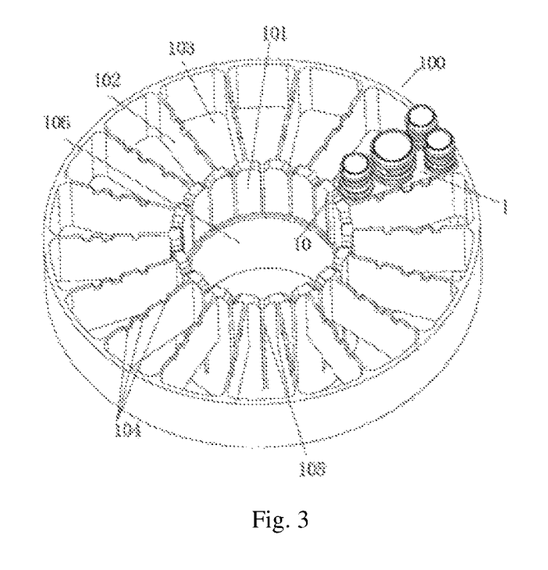
FIG. 3 is a schematic diagram illustrating that reagent kits are put into a reagent kit bracket.

The reagent kit bracket 100, as shown in FIG. 3, includes an inner ring 101 and partitioning plates 102; the partitioning plates are mounted to the inner ring; a admission cavity 103 of which the horizontal cross section is an annular sector is formed between every two partitioning plates 102; and the admission cavity is used for storing a reagent kit 1. In one embodiment, the number of the admission cavities 103 is configured such that a maximum number of reagent kits can be contained in the reagent kit bracket. Due to this configuration, more test items can be accomplished, and reagent kits do not need to be placed twice in a series of tests.

In one embodiment, positioning slots 104 are formed in the upper edge of each partitioning plate 102 of the reagent kit. Positioning parts 7 are arranged at locations on the reagent kit as shown in FIG. 2 corresponding to the partitioning plate positioning slots 104. Before the reagent kit is put into the admission cavity of the bracket, the reagent kit positioning parts are aligned to the positioning slots, and then, the reagent kit is fed into the admission cavity downwards, thus ensuring that the reagent kit can be accurately contained inside the admission cavity 103, so as to guarantee a liquid acquirer of the analyzer can be accurately fed into the reagent storage cavity or the mixing cavity when the reagent is acquired in the test process, thereby preventing the liquid acquirer from touching the upper cover of the reagent kit to cause damage to the liquid acquirer. In another embodiment, to reduce the weight of the analyzer, each admission cavity of the reagent kit bracket is vertically cut through, and the bottom of the admission cavity is not provided with a bottom plate for supporting the reagent kit. Therefore, the positioning parts and the positioning slots are matched with each other to support the reagent kit placed inside the admission cavity 103. The longitudinal depth of the positioning parts 7 is identical to the depth of the positioning slots 104. After the reagent kit is put into the admission cavity, if the upper surface of the positioning part is flush with the upper surface of the positioning slot, it means that the reagent kit is arranged in place, and the operation requirement of the analyzer is met. In embodiments as shown in FIGS. 1 to 3, the upper surfaces 71 of the positioning parts 7 are flush with the upper surface 8 of the reagent kit, and the depth of the positioning slots 104 is identical to the longitudinal depth of the positioning parts 7. After the reagent kit positioning parts are inserted along the positioning slots, if the upper surfaces 71 of the positioning parts are flush with those of the positioning slots, it means that the reagent kit is arranged in place. Due to the design that the upper surfaces 71 of the positioning parts 7 are flush with the upper surface 8 of the reagent kit, an operator is capable of observing whether the reagent kit is arranged in place more conveniently.

Figure 4:
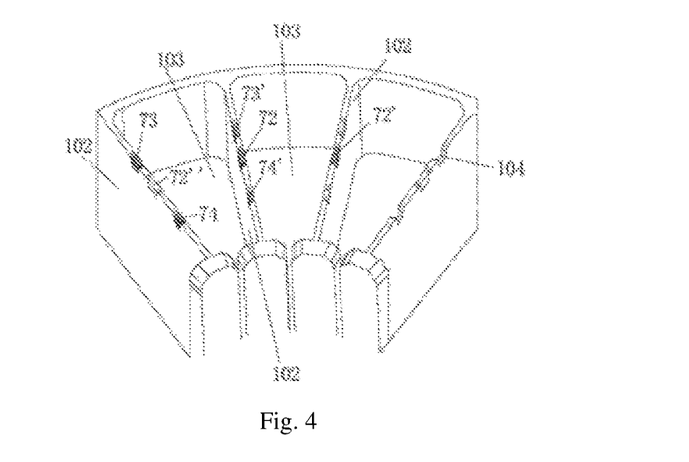
FIG. 4 is a schematic diagram showing the matching between positioning parts arranged in a staggered manner with positioning slots on the bracket.
Figure 5:
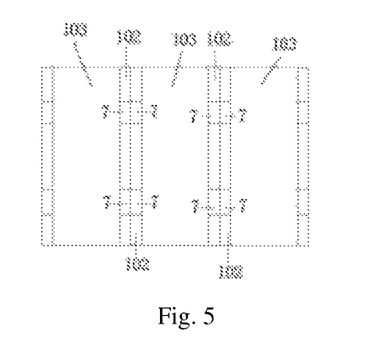
FIG. 5 is a schematic diagram showing the matching between positioning parts arranged in a corresponding manner with positioning slots on the bracket.
Figure 6:
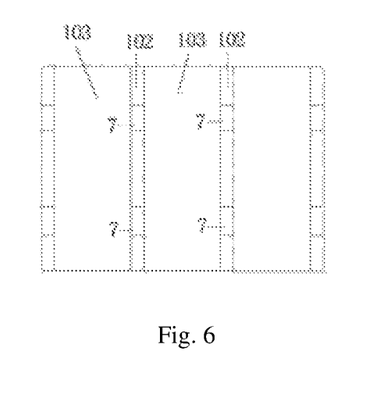
FIG. 6 is a schematic diagram showing the matching between positioning parts arranged on only one side wall of the reagent kit and positioning slots on the bracket.

In one embodiment, positioning parts on two side walls of a reagent kit are arranged alternately. Specifically, a positioning part is arranged on the first side wall of the reagent kit, and a positioning part on the second side wall of the reagent kit is not arranged at a position corresponding to the positioning part on the first side wall. Further, as shown in FIG. 1, a middle positioning part 72 is arranged on one side wall of the reagent kit, and another side wall of the reagent kit includes a left positioning part 73 and a right positioning part 74; the left positioning part and the right positioning part are respectively positioned on two corresponding sides of the middle positioning part. As shown in FIG. 4, according to a method of the embodiment, three partitioning plates 102 with an identical arrangement of positioning slots 104 form two admission cavities 103; after being put into the admission cavities, two reagent kits 1 with an identical arrangement of positioning parts tightly lean against two sides of the same partitioning plate. The middle positioning part 72 of the first reagent kit, and the left positioning part 73 and the right positioning part 74 of the second reagent kit are matched with the corresponding partitioning plate positioning slots alternately. The left positioning part 73 and the right positioning part 74 of the first reagent kit, and the middle positioning part 72" of the third reagent kit are matched with the corresponding partitioning plate positioning slots alternately. The middle positioning part 72 of the second reagent kit and the left positioning part and the right positioning part of the fourth reagent kit are arranged alternately. Due to the design solution, the number of partitioning plates can be reduced, so that the size of the analyzer can be reduced. In addition, as two side walls of each reagent kit are supported by the partitioning plates, storage stability of the reagent kit inside the admission cavity is ensured. Compared with the design of FIG. 5, the embodiment as shown in FIG. 4 illustrates that once two reagent kits are stored, one partitioning plate of the reagent kit bracket can be reduced, therefore, the space occupied by the reagent kit bracket can be reduced, and a larger space can be available to store more reagent kits as the number of the partitioning plates of the reagent kit bracket is reduced. The positioning parts 7 on two side walls of the reagent kit as shown in FIG. 5 are arranged corresponding to each other, and when two reagent kits are put into the admission cavities, four partitioning plates 102. Compared with the design of FIG. 6, the embodiment of FIG. 4 illustrates that the reagent kits are stored more stably. As shown in FIG. 6, to hold two reagent kits inside containing cavities formed by three partitioning plates, only one side wall of each reagent kit is provided with the positioning parts 7. After the reagent kits are put into the admission cavities 103, the side edges of the reagent kits without the positioning parts are not supported by the partitioning plates 102, so that the placement of the reagent kits in the admission cavities is very unstable.

The inner ring of the reagent kit bracket may further include reagent kit positioning guiding slots 105, and a reagent kit is provided with a guiding part 9. When the reagent kit is put into the admission cavity, the guiding part 9 is inserted into the guiding slot 105 and moves downwards along the guiding slot. Due to the matching design of the guiding slot and the guiding part, the reagent kit can be rapidly and accurately put into the admission cavity. In embodiments as shown in FIGS. 2 and 3, a guiding slot 105 is positioned in the middle between every two partitioning plates; the guiding part 9 is positioned in the middle of the outer side of a narrow end of the reagent kit. In another embodiment, a stop block 10 is further mounted on the guiding part, and the width of the stop block is greater than that of the opening of the guiding slot. As shown in FIG. 3, after the guiding part 9 is inserted into the guiding slot, the stop block 10 is positioned on the outer side of the guiding slot 105, and the position of the reagent kit inside the admission cavity is further limited.

A reinforcing wall 106 may be further arranged on the inner side of the inner ring of the reagent kit bracket; the reinforcing wall 106 further ensures the shape of the reagent kit bracket, such as a circular shape. In the operation process of the analyzer, the reagent kit bracket of a stable shape can ensure accuracy of reagent sampling. After the reagent kit is put into the admission cavity, the bottom of the stop block 10 can also abut against the upper surface of the reinforcing wall 106, thus functioning to further support the reagent kit.

A reagent storing device for the full-automatic in vitro diagnosis analyzer comprises reagent kits 1 and a reagent kit bracket 100 of the present invention, wherein the reagent kit bracket includes admission cavities 103; the number of the admission cavities 103 is configured such that a maximum number of reagent kits can be contained in the reagent kit bracket; each reagent kit includes a reagent storing cavity 4 and/or a mixing cavity 3; the number and the size of the reagent storing cavity 4 and/or the mixing cavity 3 are configured such that a maximum types of reagents and/or a maximum quantity of reagents can be stored in the reagent kit. The reagent kit as shown in FIG. 1 includes three circular reagent storage cavities 4 and one mixing cavity 3 located at a narrow end of the reagent kit; a storage cavity with a larger diameter is formed in the middle of the reagent kit; two storage cavities of the same diameter are formed in parallel at a wide end of the reagent kit; the outer edges of the storage cavities and the mixing cavity are tangent to the inner wall of the reagent kit. In one embodiment, the entire reagent kit is provided with the storage cavities solely.

In one embodiment, the horizontal cross sections of the admission cavities and the reagent kits are both annular sectors. The combination of the number of the admission cavities and the number of the reagent storage cavities enables the reagent stored in the reagent storing device to reach the maximum amount of the reagent that can be stored in the reagent storing device.

In one embodiment, the reagent bottle 11 includes a clamping part, and the storage cavity 4 includes a blocking part. The blocking part is used for blocking the clamping part from leaving the storage cavity. When the clamping part is blocked by the blocking part, a reagent kit body can be lifted together with a lifted reagent bottle, so that the whole kit body is kept in balance, and the danger that the reagent is dumped because of inclination is avoided.

Figure 7:
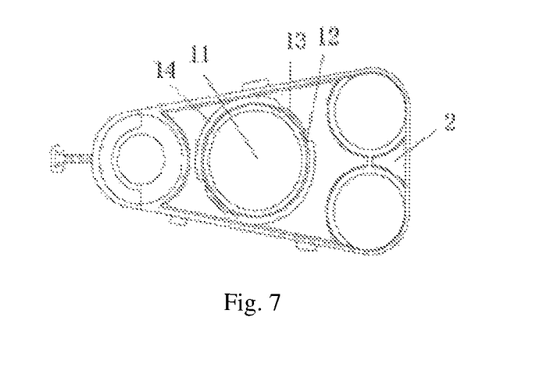
FIG. 7 is a top view illustrating that a convex block is put into a reagent kit body along a clamping part passage.
Figure 8:
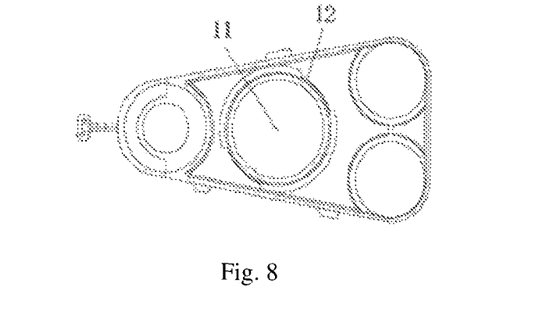
FIG. 8 is a top view illustrating that a convex block is rotated to be below a cover edge.
Figure 9:
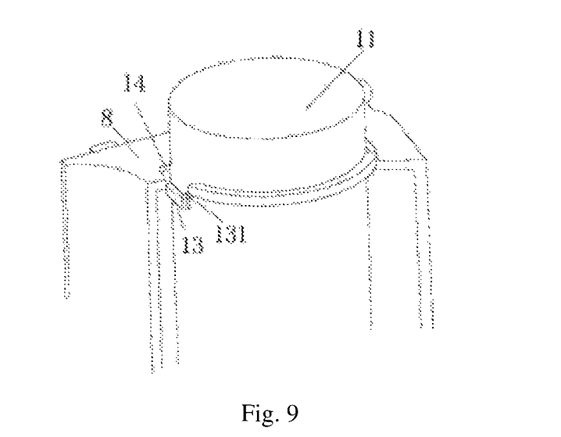
FIG. 9 is a partial view illustrating that a convex block is put into a reagent kit body along a clamping part passage.
Figure 10:
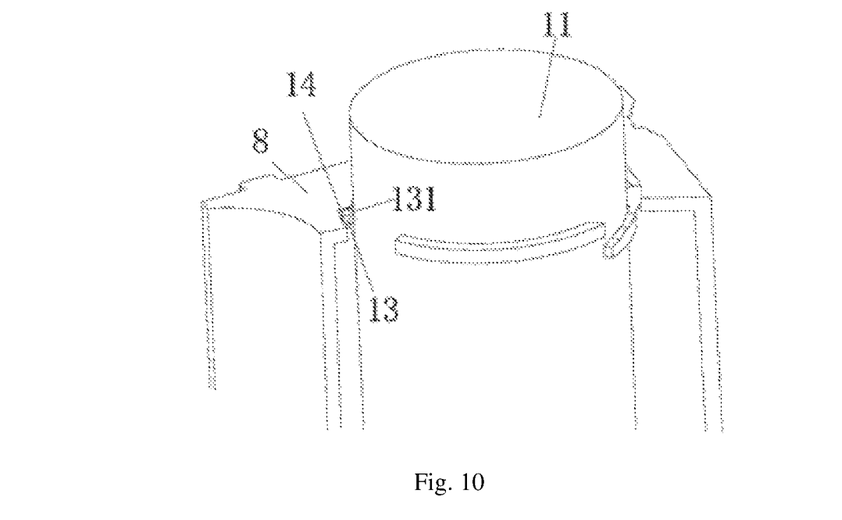
FIG. 10 is a partial view illustrating that a convex block is rotated to be below a cover edge.

In embodiments as shown in FIG. 1 and FIGS. 7 to 10, the reagent kit 1 includes a kit body 2 and a storage cavity 4. The storage cavity is used for storing a reagent or a reagent bottle containing a reagent. The reagent bottle 11 includes a clamping part; and the storage cavity 4 includes a blocking part and a clamping part passage 12. In one embodiment, the clamping part is a convex block 13 mounted on the outer wall of the reagent bottle; the blocking part is a cover edge 14 of a kit body cover; the cover edge is a part of the kit body cover; and the cover edge 14 is closer to the center of the transverse cross section of the storage cavity than the inner wall of the storage cavity 3. The clamping part passage 12 is positioned at the cover and is adjacent to the blocking part. The convex block 13 is fed into or leaves the storage cavity through the clamping part passage 12. As shown in FIGS. 7 and 9, when the reagent bottle 11 needs to be put into the kit body 1, the convex block 13 on the reagent bottle is firstly aligned to the clamping part passage 12, and subsequently the reagent bottle is put into the storage cavity downwards. As shown in FIGS. 8 and 10, after reaching a preset position, the reagent bottle is rotated, the convex block 13 (namely, the clamping part) on the reagent bottle is rotated to the part below the cover edge 14 (namely, the blocking part), and then the reagent bottle cannot be moved out of the kit body. When the reagent bottle is lifted up, the kit body is also lifted up, and then the reagent kit can be put into an analysis instrument or can be taken out of the analysis instrument. When the reagent bottle is rotated to rotate the convex block to the clamping part passage 12, the convex block 13 is not positioned below the cover edge 14 any longer, so that the reagent bottle can be moved out of the kit body. In a preferred solution, the tail end of the convex block includes a stop part 131, and the stop part is higher than the lower bottom surface of the cover edge. When the convex block is rotated to be below the cover edge, the stop part cannot pass through the cover edge, which indicates that the convex block is rotated in place.

Figure 11:
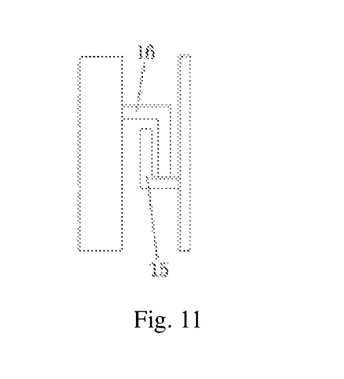
FIG. 11 is a schematic diagram showing the matching between an L-shaped structure part on a reagent bottle and an inverted concave structure inside a kit body.

In an embodiment as shown in FIG. 11, the clamping part is an L-shaped structural part 15, and the blocking part is an inverted concave structural part 16. When the reagent bottle reaches a preset position, the reagent bottle is rotated to rotate the L-shaped structural part 15 on the reagent bottle into the inverted concave structural part 16, and then the reagent bottle cannot be taken out of the kit body. When the reagent bottle is lifted, the kit body can also be lifted up.

Figure 12:
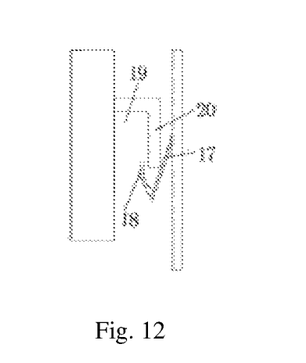
FIG. 12 is a schematic diagram showing the matching between a buckle part on a reagent bottle and a buckle groove inside a kit body.
Figure 13:
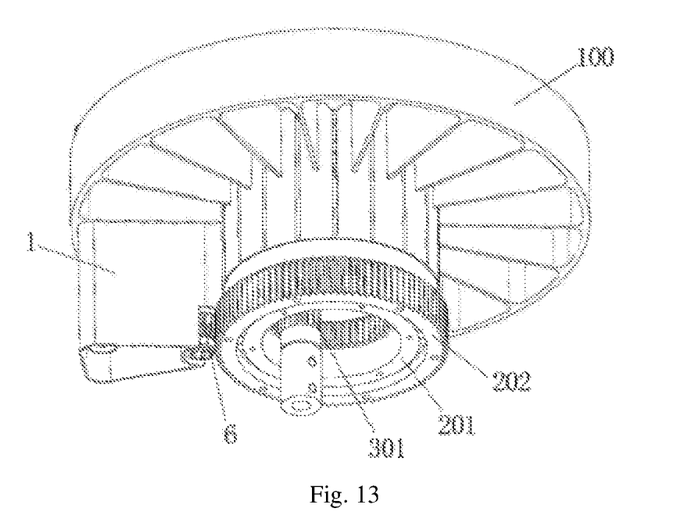
FIG. 13 is a schematic diagram showing the matching between a reagent storage device and a reagent mixing and conveying device.
Figure 14:
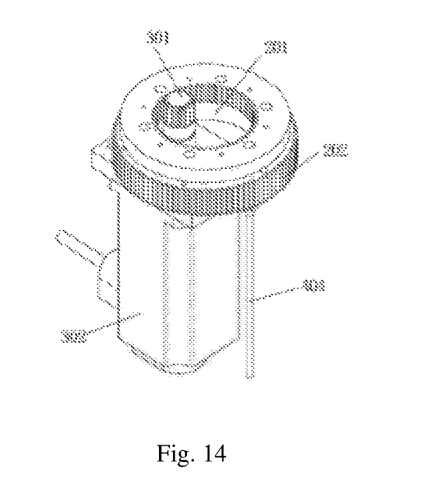
FIG. 14 is a schematic diagram of the reagent mixing and conveying device.

In an embodiment as shown in FIG. 12, the clamping part is a buckle part, which includes an elastic clamping arm 17 and a clamping foot 18, one end of the clamping arm 17 being mounted on the outer wall of the reagent bottle. The blocking part is a buckle groove 19. When the reagent bottle is stored inside the storage cavity, the clamping arm 17 is pressed to the outer wall of the reagent bottle and is moved downwards along a vertical plate 20 of the buckle groove 19 till the clamping foot 18 is buckled inside the buckle groove 19, and the vertical plate 20 of the buckle part prevents the clamping foot from moving out of the storage cavity. When the reagent bottle needs to be replaced, the reagent bottle can be taken out of the kit body by only pressing the clamping arm 17 to the outer wall of the reagent bottle again to disengage the clamping foot 18 from the buckle groove 19.

The reagent mixing and conveying device includes a transport device and a driving device; the transport device includes a conveying mechanism 201 and a mixing mechanism 202; the conveying mechanism 201 and the mixing mechanism 202 are sleeved with each other to form a bearing structure; the conveying mechanism is used for holding reagent kits and conveying the reagent kits to a corresponding position of the analyzer; the mixing mechanism 202 is matched with a rotating part 6 and is used for mixing a reagent to be uniformly mixed inside the reagent kits; the driving device includes a driving end 301 and a power part 302; the driving device drives the conveying mechanism 201 to move relative to the mixing mechanism, and enables the rotating part 6 for mixing the reagent to be in transmission with the mixing mechanism 202, so as to achieve transferring and uniform mixing of test reagent.

Figure 15:
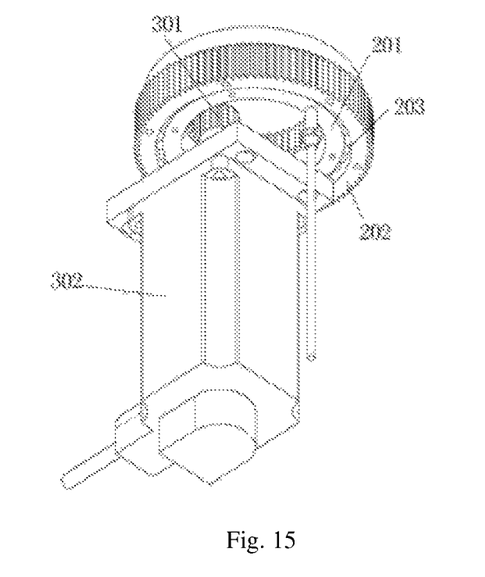
FIG. 15 is a schematic diagram of the reagent mixing and conveying device.
Figure 16:
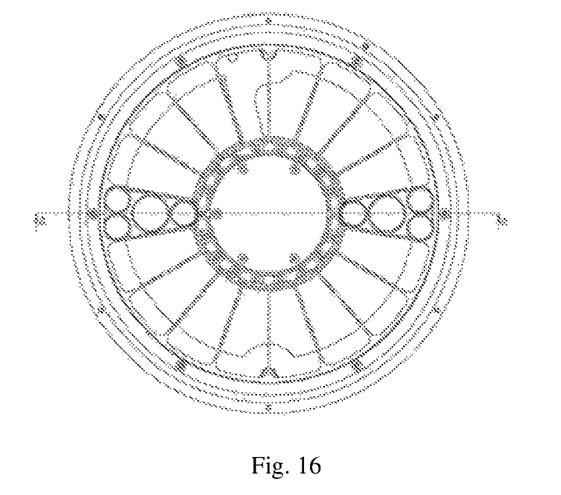
FIG. 16 is a top view of a reagent cabin.
Figure 17:
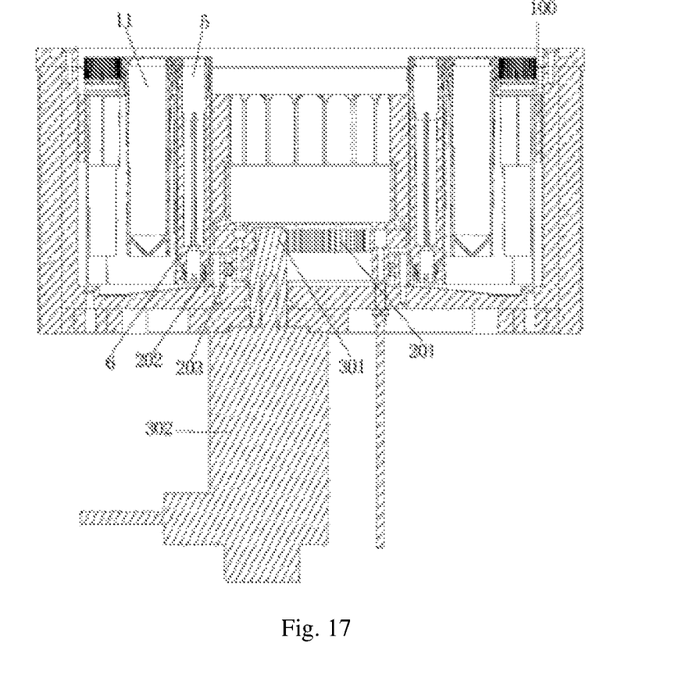
FIG. 17 is a sectional view of the reagent cabin of FIG. 16 in an A-A direction.

In embodiments as shown in FIGS. 13 to 17, the conveying mechanism 201 and the mixing mechanism 202 are of annular structures; the conveying mechanism is arranged in the central hole of the mixing mechanism; and the conveying mechanism 201 and the mixing mechanism 202 are assembled together to form a bearing structure. In an embodiment as shown in FIG. 15, beads 203 are arranged between the conveying mechanism 201 and the mixing mechanism 202. The mixing mechanism is fixedly mounted on the analyzer. The driving end 301 of the driving device is arranged in a central hole of the conveying mechanism. In one embodiment, the conveying mechanism 201 is of an internal gear structure; the mixing mechanism 202 is of an external gear structure; the driving end 301 is provided with a driving rack; the driving rack is engaged with the internal gear of the conveying mechanism; and the power part 302 is a motor. The reagent kit mixing cavity as shown in FIG. 2 includes a mixing reagent bottle 5 with a rotating part 6 at the bottom; the reagent bottle is filled with a magnetic particle reagent to be mixed; and the rotating part 6 is of a gear structure. When the reagent kit 1 is placed on the conveying mechanism 201, the gear (the rotating part) mounted at the bottom of the reagent bottle is engaged with the external gear of the mixing mechanism 202. The motor is powered on to rotate the driving end, the conveying mechanism is driven by the driving end to rotate, and the reagent kit placed on the conveying mechanism is also rotated together, so that the gear is in transmission with the external gear of the mixing mechanism. The reagent bottle with the rotating part at the bottom autorotates under the engagement transmission of the mixing mechanism and the rotating part, so that the reagent inside the reagent bottle can be uniformly mixed under rotation. In the embodiment, the mixing mechanism is fixedly mounted on the analyzer, the mixing mechanism cannot rotate, and the conveying mechanism is rotated along a central shaft of the mixing mechanism. In another solution, the conveying mechanism and the mixing mechanism may also rotate relatively along the same central shaft.

The transmission mode between the driving end 301 and the conveying mechanism 201 can also be selected from gear engagement transmission, friction transmission and belt pulley transmission; and the transmission mode between the mixing mechanism 202 and the rotating part 6 can also be selected from gear engagement transmission and friction transmission.

The conveying mechanism and the mixing mechanism are assembled together in the form of a bearing structure, so that the friction coefficient of the conveying mechanism and the mixing mechanism in the movement process can be reduced, the mechanical noise of an operating machine can be reduced, the operation energy consumption of the analyzer can be reduced, and the service life of the analyzer can be prolonged. Compared to the prior art that the conveying mechanism and the mixing mechanism need to be mounted to the analyzer in separate steps respectively, the conveying mechanism and the mixing mechanism can be mounted as a whole to the analyzer in the present invention, so that the mounting operation is simple and convenient, and regular repairing, maintenance, cleaning and replacement is facilitated. In addition, it can effectively ensure horizontal planes of the conveying mechanism and the mixing mechanism are kept in parallel to each other, so that the position relationship of the conveying mechanism and the mixing mechanism can be stable, a relatively good dynamic balance state can be maintained, and the operation precision of the analyzer can be improved. In long-term operation process, the rotating part and the mixing mechanism can be stably assembled, and the teeth colliding are unlikely to occur. As the conveying mechanism and the mixing mechanism are assembled to form the bearing structure, corresponding fittings on the analyzer can be reduced, so that the mounting space of fittings of the analyzer can be saved. As the driving end is mounted in the central hole of the conveying mechanism, the available space of the analyzer is well utilized, so that the overall size of the analyzer is relatively small.

In another embodiment, the mixing mechanism 202 is arranged in the central hole of the conveying mechanism 201, and the conveying mechanism and the mixing mechanism are assembled together to form the bearing structure. The conveying mechanism 201 is of an external gear structure, the mixing mechanism 202 is of an internal gear structure, and the driving end is arranged on the outer side of the conveying mechanism.

In one embodiment, the conveying mechanism includes a base and a mounting seat; the base is positioned in the central hole of the mixing mechanism and is connected with the mixing mechanism in the form of a bearing structure; the mounting seat is mounted on the base; and the mounting seat is used for holding a reagent kit. The mounting seat includes a transmission part matched with the driving end. The mounting seat is driven by the driving end to rotate; the mounting seat causes the conveying mechanism to rotate relative to the mixing mechanism; the reagent kit placed on the mounting seat also rotates together, and thus the rotating part and the mixing mechanism are in transmission. The reagent bottle with the rotating part at the bottom autorotates under the transmission of the mixing mechanism and the rotating part, so that the reagent inside the reagent bottle is uniformly mixed under rotation. In another embodiment, the conveying mechanism does not include a transmission part matched with the driving end; the mixing mechanism does not include a transmission part matched with the rotating part; and the conveying mechanism and the mixing mechanism are assembled together to form a bearing structure. As independent components, the transmission parts, such as the gear and the friction block, are respectively mounted at corresponding positions of the conveying mechanism and the mixing mechanism.

The reagent cabin 400 of the full-automatic analyzer includes a reagent storing device and a reagent mixing and conveying device; the reagent mixing and conveying device includes a transport device and a driving device; the transport device includes a conveying mechanism 201 and a mixing mechanism 202; the conveying mechanism 201 and the mixing mechanism 202 are sleeved with each other to form a bearing structure; the reagent storing device includes a reagent kit and a reagent kit bracket; the reagent kit bracket 100 is mounted on the conveying mechanism 201; the reagent kit 1 is put into the reagent kit bracket 100; and a rotating part 6 which is connected with a reagent bottle filled with a reagent to be mixed is matched with the transmission part of the mixing 202. The driving device includes a driving end 301 and a power part 302. When the reagent mixing and conveying device is operated, the conveying mechanism 201 is driven by the driving device to move relative to the mixing mechanism, so that the reagent kit is conveyed to a corresponding position for detection. Meanwhile, with the rotation of the conveying mechanism, the rotating part for mixing a reagent is in transmission with the mixing mechanism, and the reagent bottle autorotates inside the reagent kit under the transmission of the mixing mechanism and the rotating part, so that the reagent inside the reagent bottle is uniformly mixed under rotation.

Figure 18:
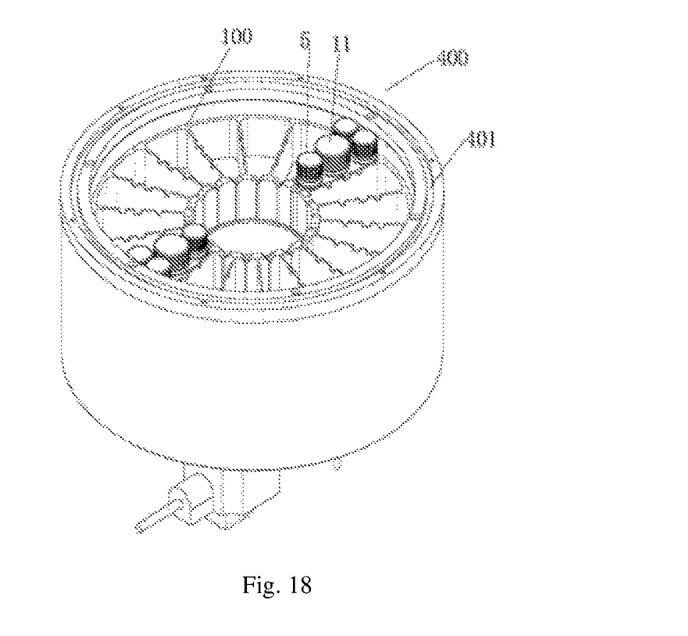
FIG. 18 is a schematic diagram of a reagent cabin with reagent kits therein.
Figure 19:
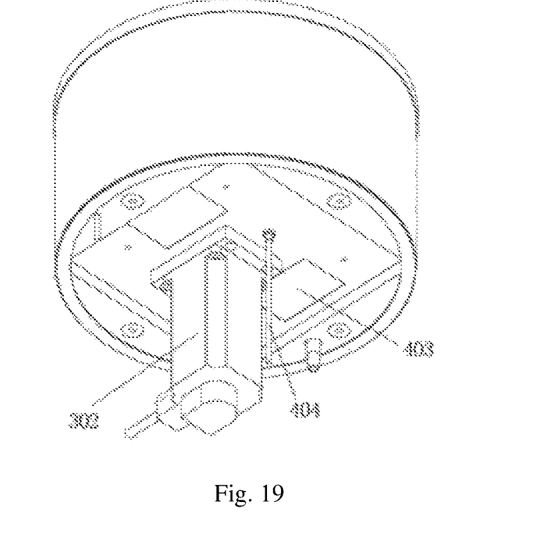
FIG. 19 is a schematic diagram of a reagent cabin with a refrigeration device.

The reagent cabin 400 as shown in FIGS. 18-19 further includes a heat preservation layer 401 and a cabin cover, so that the reagent cabin is in a relatively heat preserved and closed state; the reagent storing device is enclosed by the heat preservation layer, so that the reagent inside the reagent cabin is at a constant temperature; the reagent cabin further includes a reagent cabin refrigeration device 403 for refrigerating the reagent cabin. In one embodiment, the refrigeration device is a semiconductor refrigeration piece. In one embodiment, the refrigeration device is arranged at the bottom of the reagent cabin. The reagent cabin further comprises a reagent bottle zero position sensor 404 for determining the initial position of the reagent cabin.

A reagent mixing method of a full-automatic analyzer, which includes the following steps. First, a reagent kit with a test reagent is put into a reagent cabin, and the reagent kit is placed on a reagent kit bracket of the invention. The reagent kit bracket is matched with the reagent mixing and conveying device of the present invention. When the reagent mixing and conveying device is operated, the driving device of the full-automatic analyzer drives the conveying mechanism 201 to move relative to the mixing mechanism, and according to demands of test items, a corresponding reagent kit is conveyed to reagent acquisition position of the analyzer by the conveying mechanism. Meanwhile, with the rotation of the conveying mechanism, the rotating part for mixing a reagent is in transmission with the mixing mechanism, and the reagent bottles autorotate inside the reagent kit under the transmission of the mixing mechanism and the rotating part, so that the reagent inside the reagent bottle is uniformly mixed under rotation.

The invention claimed is:

1. A chemiluminescence immunoassay analyzer, comprising:
   a sample cabin configured to receive a test sample;
   a reagent cabin comprising a reagent mixing and conveying device comprising a transport device and a driving device, wherein the transport device comprises a conveying mechanism and a mixing mechanism sleeved with each other to form a bearing structure, and the conveying device comprises a driving device configured to move the conveying mechanism relative to the mixing mechanism.

2. A chemiluminescence immunoassay analyzer according to claim 1, wherein the reagent cabin further comprises a reagent storing device configured to receive a test kit comprising a kit body and a mixing cavity, wherein the reagent storage device comprises a test kit bracket mounted on the conveying mechanism and configured so that operation of the conveying mechanism conveys the reagent kit to a detection position within the instrument and a rotating part is matched with a transmission part of the mixing mechanism so that rotating part mixes a reagent within the mixing cavity.

3. A chemiluminescence immunoassay analyzer according to claim 2, further comprising a cuvette storage cabin configured to store one or more cuvettes prior to use in an analysis of the test sample, an incubation cabin configured to receive a cuvette from the cuvette storage cabin during the analysis of the test sample, a washing cabin configured to perform a washing procedure during the analysis of the test sample, and a test cabin configured to perform a chemiluminescent detection during the analysis of the test sample.

4. A chemiluminescence immunoassay analyzer according to claim 1, wherein the conveying mechanism and the mixing mechanism are of annular structures; and the conveying mechanism is arranged inside a central hole of the mixing mechanism.

5. A chemiluminescence immunoassay analyzer according to claim 1, wherein the driving device comprises a driving motor and a driving end; and the driving end is arranged in a central hole of the conveying mechanism.

6. A chemiluminescence immunoassay analyzer according to claim 5, wherein the transmission mode between the driving end and the conveying mechanism is selected from gear engagement transmission, friction transmission and belt pulley transmission; and the transmission mode between the mixing mechanism and the rotating part is selected from gear engagement transmission and friction transmission.

7. A chemiluminescence immunoassay analyzer according to claim 5, wherein the conveying mechanism is of an internal gear structure; the mixing mechanism is of an external gear structure; the driving end is provided with a driving rack; the driving rack is engaged with the internal gear of the conveying mechanism; the rotating part is a gear; the gear as the rotating part is engaged with the external gear of the mixing mechanism.

8. A chemiluminescence immunoassay analyzer according to claim 1, wherein the conveying mechanism comprises a base and a mounting seat; the base and the mixing mechanism are connected with each other in the form of a bearing; the mounting seat is mounted on the base; and the mounting seat comprises a transmission part matched with the driving device.

9. A chemiluminescence immunoassay analyzer according to claim 2, wherein the mixing cavity is configured to receive a reagent bottle, and the rotating part mixed the reagent within the reagent bottle within the mixing cavity.

10. A chemiluminescence immunoassay analyzer according to claim 9, wherein the reagent bottle rotates within the reagent kit under the transmission of the mixing mechanism and the rotating part, so that the reagent inside the reagent bottle is uniformly mixed under rotation.

11. A chemiluminescence immunoassay analyzer according to claim 1, wherein the reagent cabin comprises a refrigeration device.

* * * * *